United States Patent [19]

Langerman

[11] Patent Number: 5,593,436
[45] Date of Patent: *Jan. 14, 1997

[54] CAPSULAR BAG IMPLANTS WITH DUAL 360 RING STRUCTURES FOR INHIBITING POSTERIOR CAPSULAR OPACIFICATION

[76] Inventor: David W. Langerman, 99 Dutch Hill Plz., Orangeburg, N.Y. 10962

[*] Notice: The term of this patent shall not extend beyond the expiration date of Pat. No. 5,366,501.

[21] Appl. No.: 343,006

[22] Filed: Nov. 21, 1994

Related U.S. Application Data

[63] Continuation-in-part of Ser. No. 60,636, May 12, 1993, Pat. No. 5,366,501.

[51] Int. Cl.$^6$ .................................. A61F 2/14; A61F 2/16
[52] U.S. Cl. ........................................ 623/4; 623/6
[58] Field of Search ..................... 623/4, 5, 6; 606/107, 606/191

[56] References Cited

U.S. PATENT DOCUMENTS

| | | |
|---|---|---|
| 4,092,743 | 6/1978 | Kelman . |
| 4,174,543 | 11/1979 | Kelman . |
| 4,244,060 | 8/1981 | Hoffer . |
| 4,402,579 | 9/1983 | Poler ........................................ 351/160 |
| 4,439,873 | 4/1984 | Poler ........................................ 623/6 |
| 4,556,998 | 12/1985 | Siepser ..................................... 623/6 |
| 4,562,600 | 1/1986 | Ginsberg et al. ........................ 623/6 |
| 4,573,998 | 3/1986 | Mazzocco ................................ 623/6 |
| 4,608,049 | 8/1986 | Kelman .................................... 623/6 |
| 4,681,585 | 7/1987 | Sayano et al. ........................... 623/6 |
| 4,704,123 | 11/1987 | Smith ....................................... 623/6 |
| 4,795,460 | 1/1989 | Anis ......................................... 623/6 |
| 4,806,382 | 2/1989 | Goldberg et al. ........................ 427/2 |
| 4,863,463 | 9/1989 | Tjan ......................................... 623/6 |
| 4,888,016 | 12/1989 | Langerman .............................. 623/6 |
| 4,963,148 | 10/1990 | Sulc et al. ................................ 623/6 |
| 5,108,429 | 4/1992 | Wiley ....................................... 623/6 |
| 5,180,390 | 1/1993 | Drews ...................................... 623/6 |
| 5,275,624 | 1/1994 | Hara et al. ............................... 623/6 |

FOREIGN PATENT DOCUMENTS

| | | | |
|---|---|---|---|
| 1597188 | 10/1990 | U.S.S.R. | ..................................... 623/4 |
| 2081469 | 2/1982 | United Kingdom . | |

OTHER PUBLICATIONS

"Chip" Posterior Chamber Lens Investigational Device Specification Sheet (date unknown) by Domilens, Inc., Laguna Hills, CA.

*Primary Examiner*—Mary Beth Jones
*Attorney, Agent, or Firm*—Norbert P. Holler; Gottlieb, Rackman & Reisman, P.C.

[57] ABSTRACT

A posterior capsular opacification-inhibiting device designed for in-the-bag implantation has a pair of 360° concentric endless rings having different diameters and interconnected by bridging elements disposing the plane of the outer ring anteriorly offset relative to the plane of the inner ring. The outer diameter of the outer ring is slightly larger than the inner diameter of the capsular bag at the equator thereof. When the device is properly implanted, the outer ring presses against the interior surface of the equatorial region of the capsular bag without unfurling the anterior capsular flap of the latter and constitutes a primary mechanical barrier to the migration of epithelial cells from the equatorial region toward the optic region of the posterior capsule, while the inner ring presses against the anterior surface of the posterior capsule a short distance away from the equatorial region and constitutes a secondary mechanical barrier to the migration of epithelial cells which may not have been blocked by the primary barrier, thereby to inhibit capsular fibrosis and posterior capsular opacification.

16 Claims, 3 Drawing Sheets

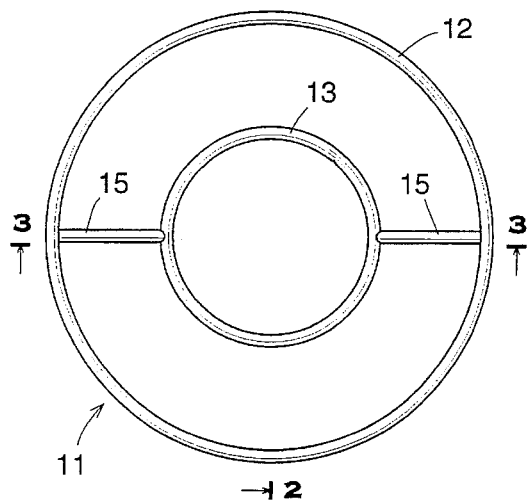
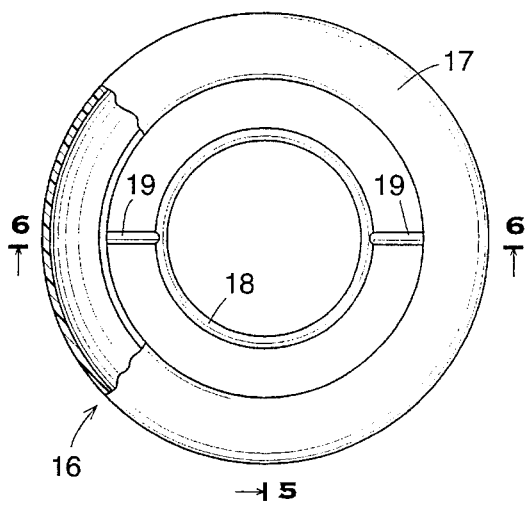
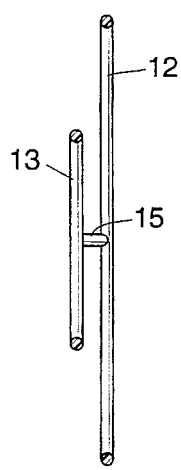
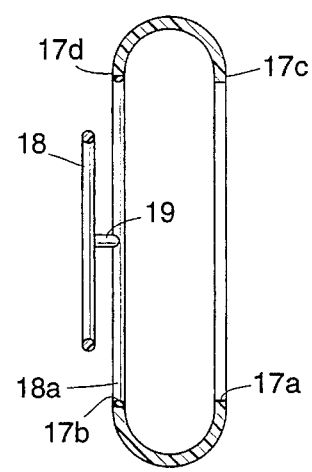
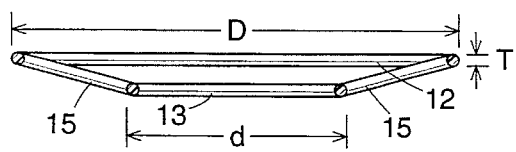
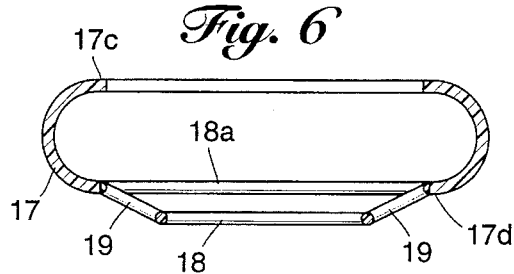

CAPSULAR BAG IMPLANTS WITH DUAL 360 RING STRUCTURES FOR INHIBITING POSTERIOR CAPSULAR OPACIFICATION

CROSS-REFERENCE TO RELATED APPLICATION

This application is a continuation-in-part of my prior U.S. patent application Ser. No. 08/060,636, filed May 12, 1993, now U.S. Pat. No. 5,366,501 issued Nov. 22, 1994, and entitled "Intraocular Lens With Dual 360° Haptics."

INTRODUCTION

This invention relates to posterior chamber implants, and in particular to such devices which are designed for in-the-bag implantation, i.e., implantation in the residual capsular bag of an eye, following an extracapsular cataract extraction. To the extent necessary for an understanding of the present invention, the background disclosures of the aforesaid prior application, if not fully set forth herein, are incorporated herein by this reference.

BACKGROUND OF THE INVENTION

Human beings, especially elderly persons, frequently tend to lose vision due to a gradually increasing clouding of the natural lens of the eye, which results from the development of a degree of opacity or clouding of the fibers (the cortex) surrounding the inert nucleus of the natural lens within the capsular bag housing the same, i.e., between the anterior and posterior capsules of the bag (the anterior capsule is the wall of the bag which is closer to the cornea, and the posterior capsule is the wall of the bag which is closer to the retina). The condition where this opacity spreads into the center of the lens in the region behind the pupil so as to impair vision, is designated cataract. When the opacity has progressed sufficiently to cause the loss of useful functional vision, the cataract is said to be mature, and the only currently available treatment for that condition is the removal of the cataract by extraction of the natural lens from the eye and the replacement of the natural lens by an artificial lens.

Merely by way of definition, a cataract removal, if it entails an extraction of the entire lens (including the nucleus, the cortex (the fibers) and the enveloping capsular bag) as a unit, is identified as an intracapsular cataract extraction (ICCE). On the other hand, a cataract removal which entails an extraction of only the lens nucleus and the cortex from the endogenous capsular bag through an opening formed by cutting away the mid-region of the anterior capsule and leaves in place only that residual part of the capsular bag which consists of the posterior capsule and the remaining annular anterior capsular flap, is identified as an extracapsular cataract extraction (ECCE).

The usual follow-up to an ECCE is the implantation of an artificial intraocular lens (IOL) into the posterior chamber of the eye (the anterior chamber is the space between the cornea and the iris while the posterior chamber is the space between the iris and the capsular bag), with the haptics of the IOL then being seated either in the ciliary sulcus outside and just anteriorly of the residual capsular bag and posteriorly of the iris, so that the entire residual capsular bag isolates the IOL from the vitreous humor, or physically within the residual capsular bag at the equatorial region thereof where the anterior capsular flap adjoins the posterior capsule, so that only the posterior capsule of the residual capsular bag isolates the IOL from the vitreous humor. There are, of course, many types of IOLs, designed for implantation into either the anterior chamber or the posterior chamber of the eye, which over the years have been developed and available to eye surgeons for use in cataract surgery (representative ones are shown in Kelman U.S. Pat. Nos. 4,092,743, 4,174,543 and 4,608,049; Hoffer U.S. Pat. No. 4,244,060; Poler U.S. Pat. No. 4,402,579; Siepser U.S. Pat. No. 4,556,998; Ginsberg et al. U.S. Pat. No. 4,562,600; Mazzocco U.S. Pat. No. 4,573,998; Sayano et al. U.S. Pat. No. 4,681,585; Smith U.S. Pat. No. 4,704,123; Anis U.S. Pat. No. 4,795,460; Goldberg et al. U.S. Pat. No. 4,806,382; and Choyce U.K. Pat. No. 2,081,469), but since the designs and other features of most of these lenses are by and large not germane to the present invention, they will not be further discussed in detail herein.

While posterior chamber IOLs have proven to be of great benefit to persons who have undergone an ECCE, some post-operative complications do occasionally arise in connection therewith. As mentioned in my prior application Ser. No. 08/060,636, one such complication is a post-implantation clouding of the posterior capsule which is a consequence of the fact that some epithelial cells are almost invariably left in the equatorial region of the capsular bag and not removed therefrom during the irrigation and aspiration phase after the surgeon has extracted the cataract. These cells have a tendency to migrate over the anterior surface of the posterior capsule toward the center or optic region thereof and, upon accumulating there, lead to capsular fibrosis and the formation of Elschnig's pearls, which in turn causes opacification of the posterior capsule and ultimately impairs vision in the same manner as the original cataract did, namely, by blocking the passage of light through the capsule to the retina. To remedy this situation, a further surgical procedure then becomes necessary, which may involve scraping and cleaning the accumulated fibers from the anterior surface of the posterior capsule behind the implanted IOL and possibly even a cutting out of the opacified region of the posterior capsule by means of a laser capsulotomy (which of late has substantially supplanted knife discission as the standard operating procedure). In any event, the possibility that the patient may be traumatized or even develop retinal detachment by such a procedure, coming after the patient has already gone through two losses of vision and one or two surgical procedures (the ECCE and the IOL implantation), is a prospect to be avoided.

The problems of capsular fibrosis and formation of Elschnig's pearls and of the resultant opacification of the posterior capsule following an ECCE have been recognized in the technical and patent literature; see, for example, the discussions thereof in the aforementioned U.S. Pat. Nos. 4,244,060 (Hoffer) and 4,562,600 (Ginsberg et al.). However, neither the ridged Hoffer lens nor the flanged Ginsberg lens described in those patents has been successful in eliminating these problems, in essence for the reason that in each of these lens designs one or more recesses are formed in the ridge or flange which projects posteriorly from the lens optic and is in contact with the front or anterior surface of the IOL has been implanted. Hoffer taught that such recesses (which are designated by reference numeral 34 in U.S. Pat. No. 4,244,060) are useful because they facilitate performance of a knife discission of a clouded posterior capsule without necessitating a dislodgement of the IOL. Ginsberg et al. taught that such recesses (which are designated by reference numerals 34 and 36 in U.S. Pat. No. 4,562,600) are useful because they facilitate rotational positioning of the IOL during the initial implant surgery and also minimize the post-implantation occurrence of unwanted and disturbing light reflections into the visual field. However, such recesses constitute breaches or gaps in the ridge or flange element of the lens which actually permit that which the ridge or flange of the lens is nominally intended to inhibit, namely, the migration of the epithelial cells into the optic region of the posterior capsule from the equatorial region of the capsular bag. The Hoffer patent evidences no awareness of this problem at all and thus offers no solution therefor whatsoever, while the Ginsberg et al. patent, though recognizing the possibility of cell migration through the notch-like recesses in the lens flange, suggests only the substitution of somewhat smaller indentations or of round holes for the notches, which still leaves one or more gaps in the flange through which cells can migrate.

In both the Hoffer and Ginsberg lenses, furthermore, the ability of the epithelial cells to migrate from the equatorial region of the capsular bag toward the optic region of the posterior capsule is not inhibited in any way until the cells are practically in the optic region, i.e., when they reach the zone of contact of the ridge or flange with the posterior capsule. In the Hoffer lens, on the one hand, this is so because the hairs constituting the haptic structure of the lens, though they are received in the cleft or fornix of the capsular bag, do not exert mechanical pressure on the entire interior surface of the equatorial region of the bag. Thus, not only are there many locations where the cells are not killed by mechanical pressure, but the Hoffer lens actually relies of the presence of the cells and the resultant fibrosis to anchor the IOL in the capsular bag. At the same time, the haptic structure, by virtue of the very nature of the hairs, cannot ensure that the rim portions and the ridge of the lens are pressed against the posterior capsule to block the migration of the epithelial cells into, and hence the propagation of capsular fibrosis and the formation of Elschnig's pearls in, the optic region of the posterior capsule. In the Ginsberg lens, on the other hand, the haptics cannot even partially inhibit cell migration because they are seated in the ciliary sulcus outside the capsular bag, while at the same time they cannot fully ensure adequate pressure contact between the flange of the IOL and the posterior capsule, so that again capsular fibrosis and pearl formation are not inhibited. Moreover, by virtue of the fact that in both the Hoffer lens and the Ginsberg lens there is an open space defined between the posterior capsule and the rear or posterior face of the optic, pearl formation in the optic region of the posterior capsule is not only not inhibited but is actually promoted. Of course, even were the haptics of the Ginsberg lens seated in the capsular bag, they would still not serve to block cell migration over the entire circumferential extent of the equatorial region of the bag.

The invention disclosed in my aforesaid prior application provided a design for a posterior capsular opacification-inhibiting posterior chamber IOL adapted for in-the-bag implantation following an ECCE. The significant characteristic of that design was the presence, in surrounding relation to a central optic, of a pair of 360° haptics constituted by two concentric endless rings of different diameters. When such an IOL is properly implanted, the outer ring, the plane of which is anteriorly offset relative to the plane of the inner ring, presses against the interior surface of the equatorial region of the capsular bag and constitutes a primary mechanical barrier to the migration of epithelial cells onto the posterior capsule and over the latter into the optic region thereof, while the inner ring presses against the anterior surface of the posterior capsule a short distance away from the equatorial region and constitutes a secondary mechanical barrier to the migration of epithelial cells into the optic region of the posterior capsule, thereby to inhibit capsular fibrosis and posterior capsular opacification. The offset between the rings also serves to maintain the posterior capsule flush and taut against the optic and thereby inhibits the formation of Elschnig's pearls on the posterior capsule.

IOLs embodying the dual 360° haptic structure of my prior invention are unitary devices which are well suited for their intended purposes. It may happen, however, that an eye surgeon, in the exercise of his or her professional judgment, will wish to be able to implant into a patient's eye a standard type of IOL. Such an IOL, however, will not be provided with means enabling migration of epithelial cells from the equatorial region of the capsular bag toward the optic region of the posterior capsule and the formation of Elsching's pearls to be inhibited. Thus, the surgeon contemplating the use of such an IOL will inevitably be faced by the surgeon's dilemma, namely, having to secure the benefit of using a standard IOL at the cost of losing the above-described advantages and benefits of the dual 360° haptic arrangement and at the risk of exposing the patient to post-operative posterior capsular opacification.

BRIEF DESCRIPTION OF THE INVENTION

It is an object of the present invention, therefore, to provide a novel and improved intraocular implant construction by means of which the aforesaid advantages of the dual 360° haptic IOLs can be achieved without a use thereof while at the same time the surgeon's dilemma can be effectively avoided.

A more specific object of the present invention is the provision of such an implant construction, which is adapted for direct implantation into the residual endogenous capsular bag following an ECCE and is characterized by a structural arrangement affording, independently of the location of the IOL, dual full 360° contacts between the implant and the capsular bag in, respectively, the equatorial region and the posterior capsule of the bag so as to constitute a circumferentially uninterrupted and unitary barrier arrangement at each of two diametrally spaced locations in relatively close proximity to the equatorial region of the capsular bag for blocking cell migration over the posterior capsule.

It will be understood, in this regard, that since inhibiting posterior capsular opacification requires the presence of the posterior capsule in the eye, the present invention is applicable only when an ECCE has been performed and is inapplicable when an ICCE has been performed.

Generally speaking, the objectives of the present invention are achieved by a device which is adapted for in-the-bag implantation following an ECCE and includes two resiliently flexible, concentric, full 360° closed and continuous ring-shaped members having different diameters. The smaller, i.e., the inner, ring member is connected to the larger, i.e., the outer, ring member by a pair of bridging elements extending generally diametrally of the two ring members. The two ring members are disposed essentially in separate planes, with the plane of the larger ring member being anteriorly offset somewhat from the plane of the smaller ring member to an extent determined by the inclination of the bridging elements relative to the planes of the ring members, and the diameter of the larger ring member at its outer periphery is somewhat, albeit only slightly, e.g., between about 0.5 mm and about 1.5 mm, larger than the interior diameter of the capsular bag in the equatorial region of the latter.

The entire device may be formed as one piece of the same material by any suitable technique, such as injection molding, lathe cutting, or the like. However, some or all of the components of the device may be formed separately, if desired even of different materials, and then interconnected by being fused or otherwise bonded to each other.

The devices according to the present invention may be made entirely of any suitable biocompatible material, for example, hyaluronic acid (including the sodium, potassium and other salts thereof), polymethylmethacrylate (PMMA), silicone, collagen, hydrogel, and the like, and the rods or bridging elements for the ring members may also be made of polypropylene (prolene). The ring members are of substantially circular configuration, with the outer ring member having an outer diameter which is, as already indicated, between about 0.5 mm and about 1.5 mm greater than the inner diameter of the capsular bag, and with the inner ring member having an outer diameter which is about 2 mm smaller than that of the outer ring member.

In accordance with one embodiment of the present invention, the device may have a form very similar to that of the dual 360° haptic arrangement of the IOL disclosed in my prior application, including two rings which are made of generally rod-shaped material and are disposed in parallel planes, with the outer or larger of those rings being connected with and offset anteriorly relative to the inner or smaller ring through the intermediary of two small rod-like bridging elements extending therebetween. Upon implantation of such a device into the residual capsular bag, when the outer ring member engages the interior surface of the bag in the equatorial region thereof and presses against the same so as to provide the desired primary barrier to migration of epithelial cells onto and toward the optic region of the posterior capsule, the inner ring member engages the anterior surface of the posterior capsule and presses against the same a short distance (e.g., 2 mm) from the outer ring member so as to provide the desired secondary barrier to migration, over the posterior capsule and toward the optic region of the latter, of any epithelial cells that were not blocked by the outer ring member. The subsequently separately implanted IOL in this case will then be located anteriorly of the outer ring, with the haptics of the IOL being seated in the fornix of the capsular bag essentially adjacent the anterior surface of the outer ring.

In accordance with another embodiment of the invention, the outer ring member of the implantable device may be differently configured so as to have the form of a generally toroidally shaped ring essentially resembling a both anteriorly and posteriorly incomplete capsular bag-like structure, i.e., a bag with relatively large circular openings in the mid-regions of its anterior and posterior capsule-like portions, the plane of this ring being the plane of its equatorial diameter. The inner ring member in this embodiment of the invention has, as before, the form of a ring made of generally rod-shaped material and is connected with the toroidal outer ring through the intermediary of small rod-like bridging elements extending between the smaller ring and either the inner peripheral boundary edge of the annular posterior capsular flap-like portion of the toroidal ring or an auxiliary ring which, like the mentioned smaller ring, is made of generally rod-shaped material, is fused or otherwise bonded to the inner peripheral boundary edge of the annular posterior capsular flap-like portion of the toroidal ring, and has its plane parallel to the planes of the larger and smaller rings. The toroidal outer or larger ring of the device will, upon implantation of the device into the residual capsular bag, be received in and bear against the equatorial region of the bag and will serve as a receptacle or carrier for the subsequently implanted IOL, which function will be especially significant in the event the equatorial region of the bag has been weakened or even torn during the removal of the cataract. At the same time, the toroidal outer ring, by virtue of its equatorial outer diameter being somewhat greater than that of the bag, will not only create the primary barrier against cell migration over the posterior capsule but will also keep the bag from collapsing or shrinking, thereby preventing decentration of the subsequently implanted IOL. Also, by virtue of the equatorial plane of the toroidal ring being anteriorly offset relative to the plane of the inner or smaller ring, the latter will be pressed against the anterior surface of the posterior capsule of the bag and thus will, in accordance with the principles of the present invention, constitute the secondary barrier to cell migration over the posterior capsule.

In accordance with yet another embodiment of the invention, the device may be composed of a toroidally shaped ring as and for the purposes previously described and a relatively shallow, frusto-conical, annular, inwardly directed flange or dish-shaped structure, the latter being secured at its larger base edge to the inner peripheral boundary edge of the annular posterior capsular flap-like portion of the toroidal ring. The smaller base edge of the flange, either per se or with the addition of a ring like that of the devices according to the other embodiments, constitutes the smaller ring of the device and is adapted, by virtue of the offset between its plane and the equatorial plane of the toroidal ring, to be pressed against the posterior capsule for constituting the secondary barrier against cell migration. The toroidally shaped ring and the frusto-conical flange may be made as separate elements and then fused or otherwise bonded together to form the device, or the device may be formed as a one-piece structure molded to the desired shape.

The advantages accruing from these structural characteristics will be readily comprehended. One is that, for the purpose of introducing the device into the eye, the surgeon is able to grip the outer and inner rings at the opposite sides of the device, i.e., at the 3 o'clock and 9 o'clock positions (considering the bridging elements as being located at the top and bottom of the device, i.e., at the 12 o'clock and 6 o'clock positions), and to press them inwardly. Thus, the side to side dimension of the device is effectively reduced, so that the corneal, limbal or scleral incision through which the device is inserted into the eye need only be made just slightly larger than the reduced side to side dimension of the device.

Another advantage is that once the device has been properly implanted into the residual capsular bag of the eye and the rings have reverted to their full circular configuration, which in the case of the outer or larger ring means to a diameter adapted to and just slightly greater than the equatorial diameter of the capsular bag, the larger ring presses along its entire circumference against the interior surface of the residual capsular bag in the equatorial region thereof without overstressing the latter and without engendering an unfurling of the anterior capsular flap. At the same time, by virtue of the anterior offset of the larger outer ring relative to the smaller inner ring, the latter presses along its entire circumference against the anterior surface of the posterior capsule a short distance radially inwardly of the equatorial region. The larger ring, the thickness of which may be equal to that of the smaller ring but may be different from, preferably somewhat greater than, the thickness of the smaller ring, thereby constitutes a primary mechanical barrier for inhibiting migration of epithelial cells from the equatorial region onto the posterior capsule and toward the optic region thereof, while the smaller ring constitutes a secondary mechanical barrier for inhibiting migration, over the posterior capsule and toward the optic region thereof, of epithelial cells that were not blocked by the larger ring.

BRIEF DESCRIPTION OF THE DRAWING

The foregoing and other objects, characteristics and advantages of the present invention will be more fully understood from the following detailed description of various embodiments thereof when read in conjunction with the accompanying drawing, in which:

FIG. 1 is a plan view of a posterior capsular opacification-inhibiting device according to one embodiment of the present invention;

FIGS. 2 and 3 are sectional views taken, respectively, along the lines 2—2 and 3—3 in FIG. 1;

FIG. 4 is a plan view, partially broken away, of a posterior capsular opacification-inhibiting device according to a second embodiment of the invention;

FIGS. 5 and 6 are sectional views taken, respectively, along the lines 5—5 and 6—6 in FIG. 4;

DETAILED DESCRIPTION OF THE INVENTION

As a preliminary caution, it should be kept in mind, in regard to the herein set forth descriptions of the two types of cataract extractions and of the disclosed embodiments of the devices of the present invention, that the various figures of the drawings are purely diagrammatic illustrations, not drawn to scale, the purpose of which is to facilitate an understanding of those procedures and of the still to be described principles and embodiments of the present invention. The illustrations are not intended to represent in precise detail the various aspects of the physiological structures and surgical techniques involved in the different operations.

Figure 7:
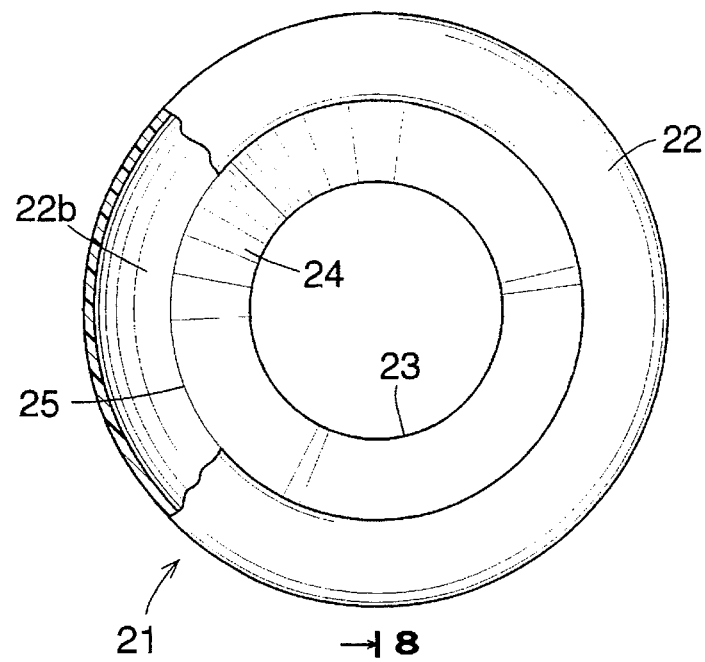
FIG. 7 is a plan view, partially broken away, of a posterior capsular opacification-inhibiting device according to a third embodiment of the invention.
Figure 8:
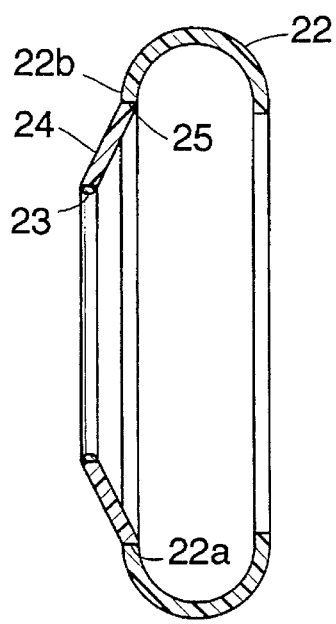
FIG. 8 is a sectional view taken along the line 8—8 in FIG. 7.
Figure 9:
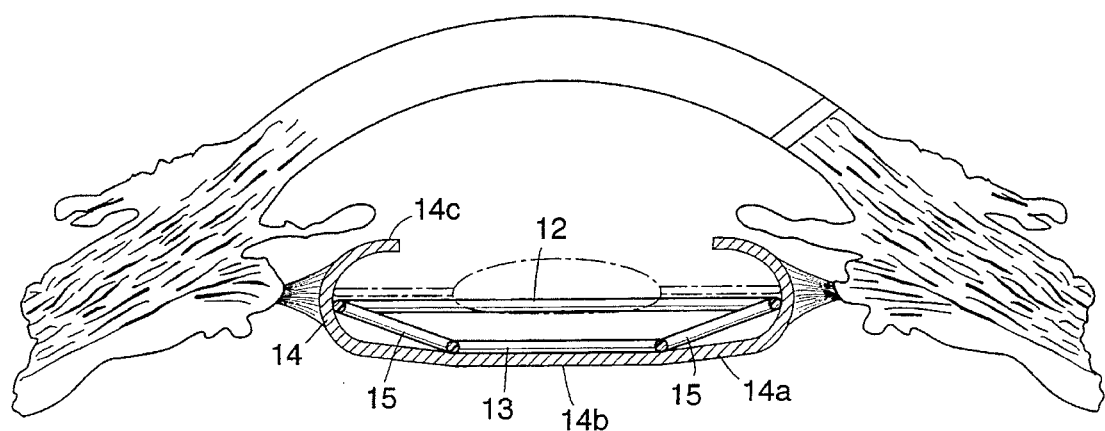
FIGS. 9 and 10 are fragmentary axial sections taken through a human eye and illustrate implantations of the devices of FIGS. 1 and 4, respectively, in the residual capsular bag of the eye following an extracapsular cataract extraction.

Referring now to the drawing in greater detail and in particular to FIGS. 1–3, a posterior capsular opacification-inhibiting device 11 according to one embodiment of the present invention is there shown which includes a dual 360° or full circle ring structure consisting of a pair of closed and continuous rings 12 and 13 of different outer diameters D and d (see FIG. 3), of which the diameter D is just slightly larger than the inner diameter of the equatorial region or zone of the residual capsular bag 14 (see FIG. 9) into which the device 11 is to be inserted The rings 12 and 13, which have a thickness T and are resiliently flexible, are arranged concentrically with each other and with their respective planes in parallel relation to one another, with the plane of the larger outer ring 12 being anteriorly offset somewhat relative to the plane of the smaller inner ring 13. The two rings are interconnected with each other by means of a pair of straight rod-like bridging elements 15 therebetween, with both bridging elements, which are basically of the same thickness as the rings and may be either straight or curved somewhat, being arranged in a common diametral plane of the device 11.

It should be noted that the above-stated relationship between the outer diameter D of the outer ring 12 and the inner diameter of the capsular bag 14 in the equatorial region or zone thereof is of great significance in the present invention. The equatorial zone diameter of a capsular bag in the eye of a human being varies, of course, as is well known and as is to be expected, from one person to another. In general, conventional practice among ophthalmologists has been and may still be to implant in a given patient an IOL having a "length" (the maximum distance, measured diametrally of the optic, between the arched seating portions of the loops or haptics) which is up to about 3.5 mm greater than the equatorial zone diameter of the capsular bag of that patient, for the express purpose of achieving a secure seating of the IOL in the bag. Experience has shown, however, that the haptics of such IOLs exert a radial pressure on the equatorial region of the bag which can cause the anterior capsular flap thereof to be literally unfolded or unfurled with a consequent shifting of the equatorial zone of the bag in a posterior direction. Such unfurling aids the migration of epithelial cells from the equatorial region of the bag onto the posterior capsule and thus the subsequent initiation of capsular fibrosis and posterior capsular opacification.

In order to avoid these drawbacks, the present invention contemplates, as an essential aspect thereof, a proper diametral dimensioning of the outer ring 12 of the device 11 relative to the size of the capsular bag. In particular, it is contemplated that the outer diameter D of the ring 12 should be about 0.5 mm to about 1.5 mm greater than the inner diameter of the equatorial zone of the capsular bag. Thus, when the device has been properly implanted, the ring 12 will apply some radially outward pressure on the equatorial zone of the bag, not enough to cause the undesired unfurling but sufficient to kill any epithelial cells it engages. Moreover, by virtue of its uninterrupted circular form, the ring 12 applies such pressure along the entire 360° circumference thereof against the equatorial zone of the capsular bag over its full circumferential extent. The ring 12 thus constitutes a mechanical barrier against migration of those epithelial cells which it contacts onto the posterior capsule and toward the optic region thereof.

At the same time it must be appreciated, however, that the width of the equatorial zone of the capsular bag is considerably greater than the region of contact between it and the ring 12 (the thickness T of the latter is only about 0.2 mm to about 1.0 mm). As a consequence thereof it is entirely possible that there may be some epithelial cells present in the radially outermost circumferential region of the posterior capsule adjacent the equatorial zone, which not only were not removed by the surgeon during the irrigation and aspiration procedure but then were not contacted and blocked by the outer ring 12 of the implanted device 11. It is to compensate for this possibility that the inner ring 13, the thickness of which is generally in the same range (0.2 mm≦T≦1.0 mm) as that of the outer ring but may be somewhat less than the thickness of the outer ring, is provided as a part of the dual ring structure and that the plane of the outer ring 12 is anteriorly offset relative to the plane of the inner ring. The magnitude of the offset is determined by the bridging elements 15 being anteriorly inclined at an angle of about 15° to the plane of the inner ring, although the angle may be even somewhat smaller (e.g., as little as 10°) or somewhat larger (e.g., as great as 30°).

By virtue of this arrangement, the constraining force exerted on the implanted device 11 by the capsular bag at the outer ring 12 is transmitted via the bridging elements 15 to the inner ring 13 and has the effect of slightly displacing the latter in a posterior direction relative to the outer ring. As a result, the inner ring is pressed against the posterior capsule 14a a small distance (on the order of about 2 mm) radially inwardly of the equatorial zone and thereby constitutes a secondary mechanical barrier to the migration, over the posterior capsule and toward the optic region 14b thereof, of epithelial cells that were not blocked by the primary barrier, i.e., the outer ring. As can be seen from FIG. 9, when a posterior capsular opacification-inhibiting device 11 is used, the subsequently implanted IOL (shown only in phantom outline in FIG. 9) will be positioned so as to be seated in the capsular bag 14 anteriorly of the device 11 but posteriorly of the anterior capsular flap 14c.

Merely by way of example, if the capsular bag diameter of a patient is about 9.4 mm, the outer diameter D of the outer ring 12 should be in the range of about 9.9 mm to about 10.9 mm, with the outer diameter d of the inner ring 13 then being in the range of about 7.9 mm to about 8.9 mm.

The principles of the present invention can also be embodied in dual ring posterior capsular opacification-inhibiting structures differing somewhat from that shown in FIGS. 1–3. For example, the device 16 shown in FIGS. 4–6 is basically similar to the device 11 in that it has an outer ring member 17 and an inner ring member 18 interconnected with each other by diametral rod-like bridging elements 19, with the inner ring 18 and the bridging elements 19 being identical to the corresponding members 13 and 15, respectively, of the device 11. The difference between the two devices in essence resides in the fact that the outer ring member 17 of the device 16 has the form of a toroidally shaped ring resembling an anteriorly and posteriorly incomplete capsular bag-like structure, with both the anterior and posterior capsule portions of that structure having respective relatively large holes or openings 17a and 17b therein to define an annular anterior capsular flap-like portion 17c and an annular posterior capsular flap-like portion 17d. As in the first embodiment, of course, the planes of the two rings 17 and 18 are parallel to one another.

As a general proposition, the bridging elements 19 at their ends remote from the ring 18 are connected to the inner peripheral boundary edge of the annular posterior capsular flap-like portion 17d of the toroidal ring 17. Preferably, however, as shown in FIGS. 4–6, those ends of the bridging elements are connected to the toroidal ring 17 through the intermediary of an auxiliary ring 18a the plane of which is parallel to the planes of both rings 17 and 18, with the said remote ends of the bridging elements being fused or otherwise bonded to the auxiliary ring 18a and with the latter being in turn fused or otherwise bonded to the inner peripheral boundary edge of the posterior capsular flap-like portion 17d. The provision of the auxiliary ring 18a serves primarily to stiffen the connection between the inner ring 18 and the outer ring 17.

Figure 10:
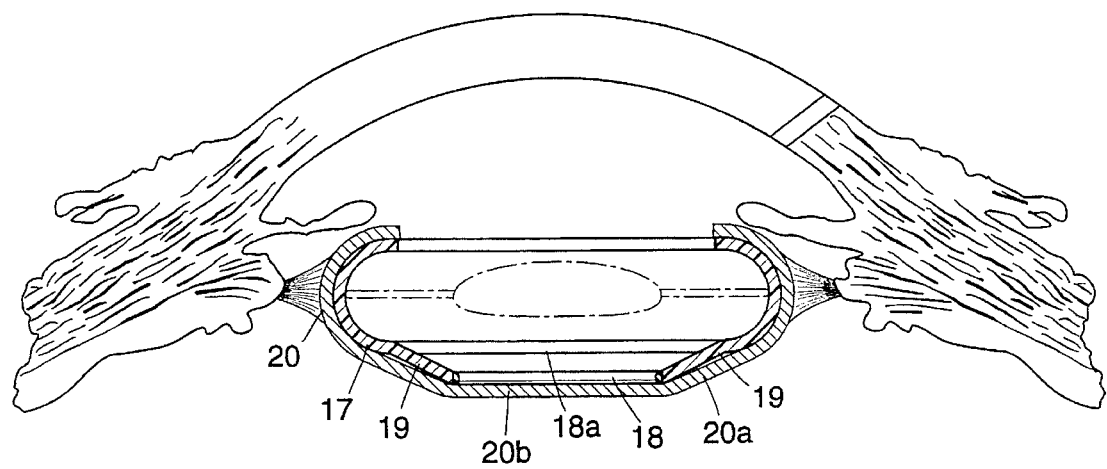

The toroidal outer or larger ring 17 is shaped as shown so that when it is properly implanted in the residual capsular bag 20 (see FIG. 10) of a patient's eye, its posterior capsular flap-like portion 17d, by virtue of its greater width or thickness relative to that of the outer ring 12 of the embodiment of the device shown in FIGS. 1–3, is at least in part in surface contact not only with the equatorial region of the capsular bag but also with the radially outwardmost region of the posterior capsule 20a (as distinguished from the line contact between the ring 12 and the equatorial region of the capsular bag). Thus, in addition to functioning (like the outer ring 12 of the first embodiment) as a means to prevent the capsular bag from collapsing or shrinking as well as a receptacle or carrier for an IOL (shown only in phantom outline in FIG. 10) to be subsequently implanted into the bag, the toroidal ring 17 at the same time performs its main function as a means constituting a primary barrier to epithelial cell migration from the equatorial region of the residual capsular bag onto the posterior capsule 20a. The ring 17, of course, also serves as a means for ensuring that the inner or smaller ring 18 will be pressed against and maintained in engagement with the posterior capsule so as to constitute a secondary barrier to migration, into the optic region 20b of the posterior capsule, of epithelial cells that were not blocked by the larger ring.

The posterior capsular opacification-inhibiting device 21 according to a third embodiment of the present invention also includes, like the device 16, a generally toroidally shaped outer ring 22 having the same structural features and functions as the ring 17. In this embodiment, however, the posterior capsule-engaging inner ring 23 of the device, the plane of which is parallel to that of the ring 22, is constituted by either the smaller base edge of an annular, relatively shallow, generally frusto-conical, inwardly directed and posteriorly slanted flange or dish-like structure 24 or by a small ring member of rod-shaped material like the rings 13 and 18 of the other embodiments secured to or incorporated in the smaller base edge of the flange. In either event, the larger base edge 25 of the flange is connected with the inner peripheral boundary edge 22a of the posterior capsular flap-like portion 22b of the toroidal ring 22 which, if desired, may also incorporate an auxiliary stiffening ring like the ring 18a of the embodiment of the device 16 shown in FIGS. 4–6. The flange 24 in the device 21 thus serves as a bridging means performing the functions of the bridging elements 15 and 19 in the devices 11 and 16. Within the contemplation of the present invention, of course, the entire device 21 can be made as a unitary or one-piece structure, or the ring member 22 and the flange 24 can be separately formed and then fused or otherwise bonded to one another.

It will be understood that the foregoing description of preferred embodiments of the present invention is for purposes of illustration only, and that the various structural and utilitarian features herein disclosed are susceptible to a number of modifications and changes none of which entails any departure from the spirit and scope of the present invention as defined in the hereto appended claims.

I claim:

1. A posterior capsular opacification-inhibiting device for implantation into an eye between the posterior capsule and the anterior capsular flap of the residual capsular bag that remains in the eye following an extracapsular cataract extraction, comprising:

a pair of resiliently flexible, concentric, closed, rings having respective planes and having different outer diameters, the larger of said rings being connected to the smaller of said rings by bridging means extending therebetween, the plane of said larger ring being parallel to but offset anteriorly from the plane of said smaller ring, and the outer diameter of said larger ring at its outer periphery being slightly larger than the inner diameter of said residual capsular bag in the equatorial region thereof;

whereby, upon proper implantation of the device into an eye, (i) said larger ring presses along its entire circumference against the interior surface of said residual capsular bag in the equatorial region thereof without overstressing the latter and without engendering an unfurling of said anterior capsular flap, said larger ring thereby constituting a primary mechanical barrier for inhibiting migration of epithelial cells from said equatorial region onto and toward the optic region of said posterior capsule of said residual capsular bag, and (ii) said smaller ring presses along its entire circumference against the anterior surface of said posterior capsule a short distance radially inwardly of said equatorial region to constitute a secondary mechanical barrier for inhibiting migration, over said posterior capsule and toward said optic region thereof, of epithelial cells that were not blocked by said larger ring.

2. A device as claimed in claim 1, wherein said bridging means comprises a plurality of bridging elements of rod-shaped configuration.

3. A device as claimed in claim 2, wherein said bridging elements are straight rods.

4. A device as claimed in claim 2, wherein said bridging elements are arcuate rods.

5. A device as claimed in claim 1, wherein said bridging means comprises a shallow frusto-conical flange inclined posteriorly relative to the plane of said larger ring and having a larger base edge and a smaller base edge, said frusto-conical flange at said larger base edge thereof being connected to said larger ring, and said frusto-conical flange at said smaller base edge thereof being connected to said smaller ring.

6. A device as claimed in claim 5, wherein said smaller base edge of said frusto-conical flange constitutes said smaller ring.

7. A device as claimed in claim 1, wherein both said rings are of generally rod-shaped cross-section.

8. A device as claimed in claim 7, wherein said bridging means comprises a plurality of bridging elements of rod-shaped configuration.

9. A device as claimed in claim 1, wherein said larger ring is of generally toroidal shape having an annular posterior capsular flap-like portion and an annular anterior capsular flap-like portion connected to each other at an outer peripheral equatorial region of said larger ring and each having an inner peripheral boundary edge, and said bridging means at one end thereof is connected to said inner peripheral boundary edge of said posterior capsular flap-like portion of said larger ring and at an opposite end thereof is connected to said smaller ring.

10. A device as claimed in claim 9, wherein said smaller ring is of generally rod-shaped cross-section.

11. A device as claimed in claim 10, wherein said bridging means comprises a plurality of bridging elements of rod-shaped configuration.

12. A device as claimed in claim 11, wherein said larger ring includes an auxiliary ring of generally rod-shaped cross-section secured circumferentially to said inner peripheral boundary edge of said posterior capsular flap-like portion of said larger ring, and said bridging elements at said one end thereof are connected to said auxiliary ring.

13. A device as claimed in claim 9, wherein said bridging means comprises a shallow frusto-conical flange inclined posteriorly relative to the plane of said larger ring and having a larger base edge and a smaller base edge, said frusto-conical flange at said larger base edge thereof being connected to said inner peripheral boundary edge of said posterior capsular flap-like portion of said larger ring, and said frusto-conical flange at said smaller base edge thereof being connected to said smaller ring.

14. A device as claimed in claim 13, wherein said smaller base edge of said frusto-conical flange constitutes said smaller ring.

15. A device as claimed in claim 13, wherein said smaller ring is of generally rod-shaped cross-section.

16. A device as claimed in claim 1, wherein the outer diameter of said larger ring is between about 0.5 mm and about 1.5 mm greater than the inner diameter of said residual capsular bag in the equatorial region thereof.

* * * * *

UNITED STATES PATENT AND TRADEMARK OFFICE
CERTIFICATE OF CORRECTION

PATENT NO. : 5,593,436

DATED : January 14, 1997

INVENTOR(S) : DAVID W. LANGERMAN

It is certified that error appears in the above-identified patent and that said Letters Patent is hereby corrected as shown below:

On the title page, in the left-hand column at item "[54]", and on the first page of the text at column 1, line 2, in each case in the title of the invention, for "DUAL 360 RING STRUCTURES" read -- DUAL 360° RING STRUCTURES --.

Signed and Sealed this

First Day of April, 1997

Attest:

BRUCE LEHMAN

Attesting Officer

Commissioner of Patents and Trademarks